US00PP32217P3

(12) United States Plant Patent
Bell et al.

(10) Patent No.: US PP32,217 P3
(45) Date of Patent: Sep. 22, 2020

(54) BLUEBERRY PLANT NAMED 'MG07876-15-003'

(50) Latin Name: ***Vaccinium* hybrid**
Varietal Denomination: MG07876-15-003

(71) Applicant: Moondarra Genetics Pty Ltd, Moondarra, Victoria (AU)

(72) Inventors: Ridley Bell, Lindendale (AU); Joel Deveson, Newborough (AU)

(73) Assignee: Moondarra Genetics PTY LTD, Moondarra (AU)

( * ) Notice: Subject to any disclaimer, the term of this patent is extended or adjusted under 35 U.S.C. 154(b) by 0 days.

(21) Appl. No.: 16/501,662

(22) Filed: May 20, 2019

(65) Prior Publication Data

US 2019/0364710 P1 Nov. 28, 2019

Related U.S. Application Data

(60) Provisional application No. 62/762,826, filed on May 22, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Plant & Planet Law Firm

(57) ABSTRACT

The new blueberry plant variety 'MG07876-15-003' is provided. 'MG07876-15-003' is a commercial variety intended for the fresh fruit market. The variety is produced from a cross of 'Elliott' and 'Caroline', which can be distinguished by its outstanding features.

3 Drawing Sheets

Latin name of the genus and species:
Genus—*Vaccinium.*
Species—hybrid.
Variety denomination: The new blueberry plant claimed is of the variety denominated 'MG07876-15-003'.

BACKGROUND OF THE INVENTION

The proposed new variety 'MG07876-15-003' was selected as a seedling from a controlled pollination involving northern highbush varieties 'Elliott' (seed parent) (not patented) and 'Caroline' (pollen parent) (not patented). The cross was made in 2007 in Moondarra, Victoria, Australia and the plant was selected in 2011 amongst a population of seedlings from the cross grown in Moondarra, Victoria, Australia. This new cultivar has been asexually propagated through cuttings since 2011 and grown in replicated field trials from 2014 in Moondarra, Victoria, Australia.

The plants of the proposed new variety 'MG07876-15-003' are strong and vigorous and self-fertile while the berries are large and firm with a moderate to good bloom, sweet flavor and a small dry scar.

SUMMARY OF THE INVENTION

The proposed new *Vaccinium* hybrid cultivar denominated 'MG07876-15-003' resulted from a cross between 'Elliott' and 'Caroline'.

The seed parent was produced by 'Burlington' (not patented) and 'US1' (not patented) and was selected based on its vigor, late fruit ripening, high yields and medium sized, frim berries with a strong flavor and bloom.

The pollen parent was produced from open pollinated 'Lateblue' (not patented) seeds sent to the Knoxfield Horticultural Research Institute in Victoria, Australia in 1976, and was selected based on its medium timing of fruit ripening, strong aromatic flavor, medium firmness and moderate bush vigor.

The proposed new variety 'MG07876-15-003' is a selection from seedlings produced from a controlled pollination between 'Elliott' and 'Caroline' in the breeding program at Moondarra, Victoria, Australia in 2007.

Asexual reproduction of the proposed new variety by cutting propagation has occurred since 2011 at Moondarra, Victoria, Australia. This has demonstrated that the new variety is uniform, stable and true to type over successive generations of asexual propagation in respect to the characteristics aforementioned.

The proposed new cultivar 'MG07876-15-003' was selected as a single plant in a population of seedlings resulting from a cross between the two northern highbush varieties previously described, selected in 2011 at Moondarra, Victoria, Australia. The selection was based upon its late period of fruit ripening, strong plant vigor and large, firm fruit with a moderate to good bloom, sweet flavor and small dry picking scar. The new cultivar was given the breeder code '5P-15-3' and evaluated in trials from 2014 to be later denominated 'MG07876-15-003'.

The following characteristics of the proposed new variety have been observed and used to distinguish 'MG07876-15-003' as a distinct cultivar of *Vaccinium* hybrid:

Round-upright/whippy growth habit.
Late timing of flowering.
Very late timing of fruit ripening.
Strong plant vigor.
Large berry size.
Small, dry picking scar
Berry firmness is firm.

The new variety differs from the seed parent 'Elliott' as previously described in terms of having later timing of fruit ripening and larger berry size. 'MG07876-15-003' differs from pollen parent 'Caroline' in respect to its later fruit ripening, firmer berries, larger berry size and stronger vigor. The proposed new variety 'MG07876-15-003' is uniform, stable and true to type over successive generations of asexual propagation through softwood cuttings in respect to the characteristics aforementioned.

BRIEF DESCRIPTION OF THE DRAWINGS

The accompanying photographic illustration shows typical specimens in full color of the foliage and fruit of the new variety 'MG07876-15-003'. The colors are as nearly true as is reasonably possible in a color representation of this type.

Figure 1:
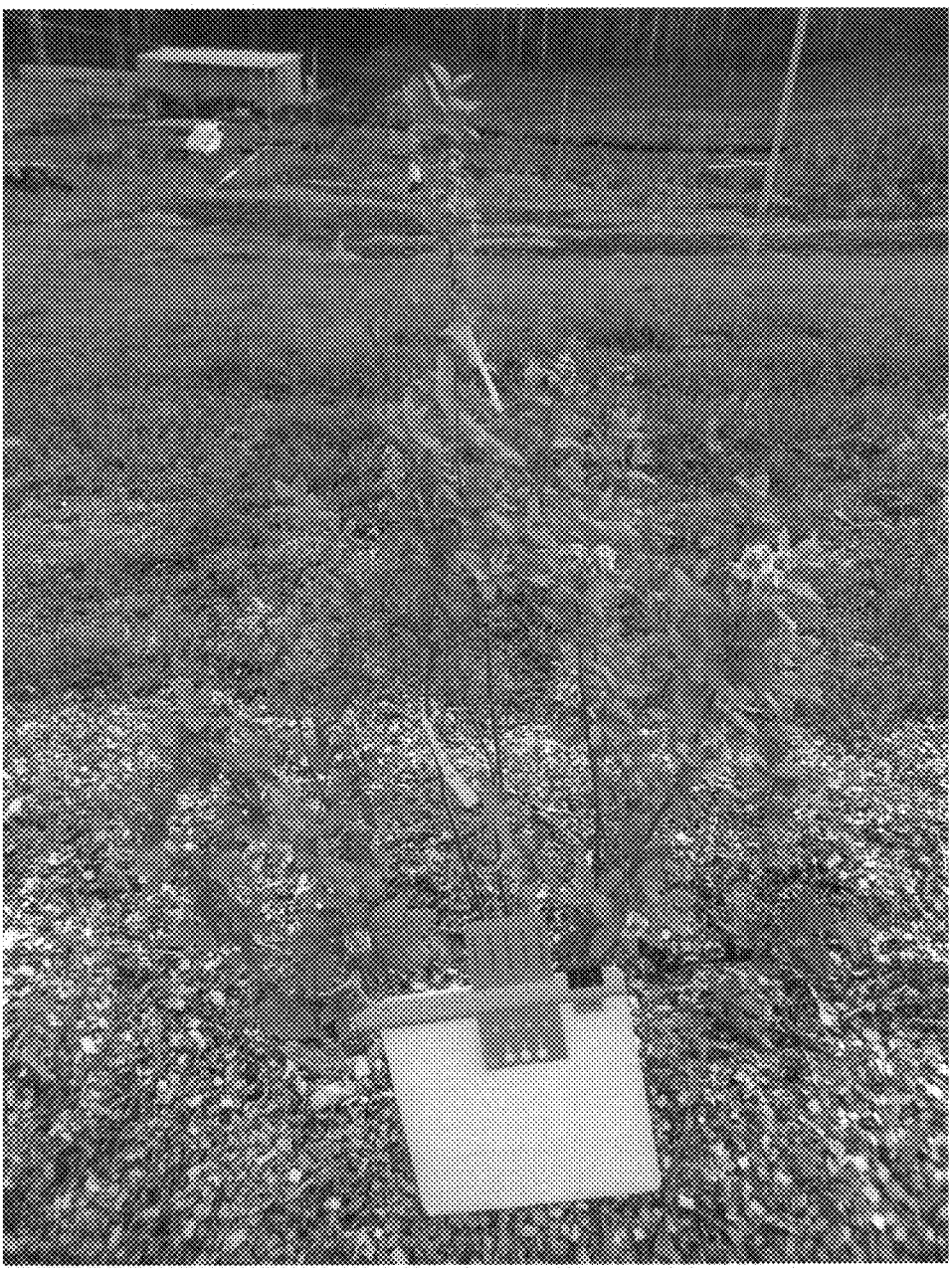
FIG. 1 is a photograph of the new variety 'MG07876-15-003', demonstrating the plant's upright growth habit at approximately 6 years of age.
Figure 2:
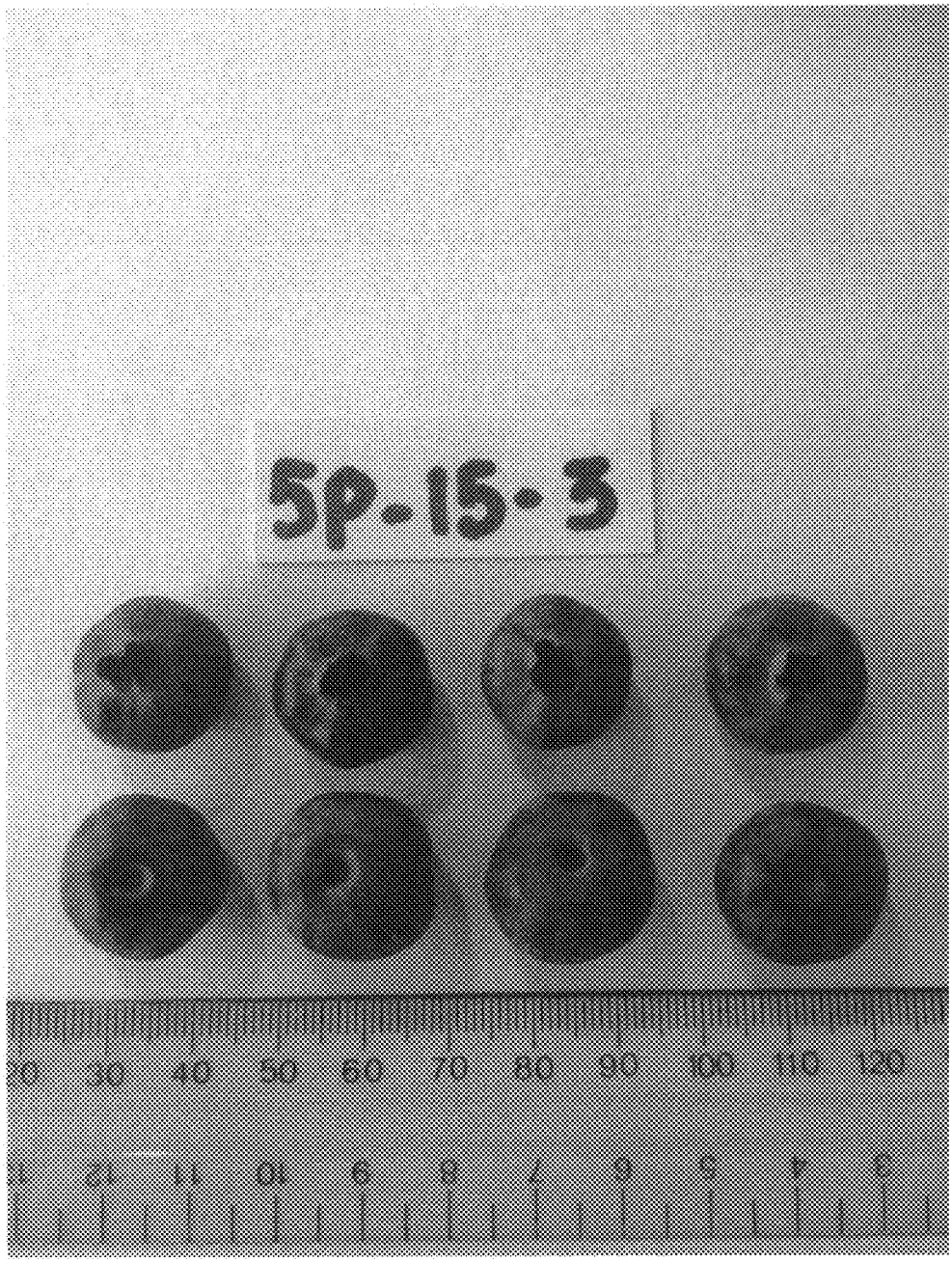
FIG. 2 is a photograph of the fruit of the new variety 'MG07876-15-003' at approximately 6 years of age.
Figure 3:
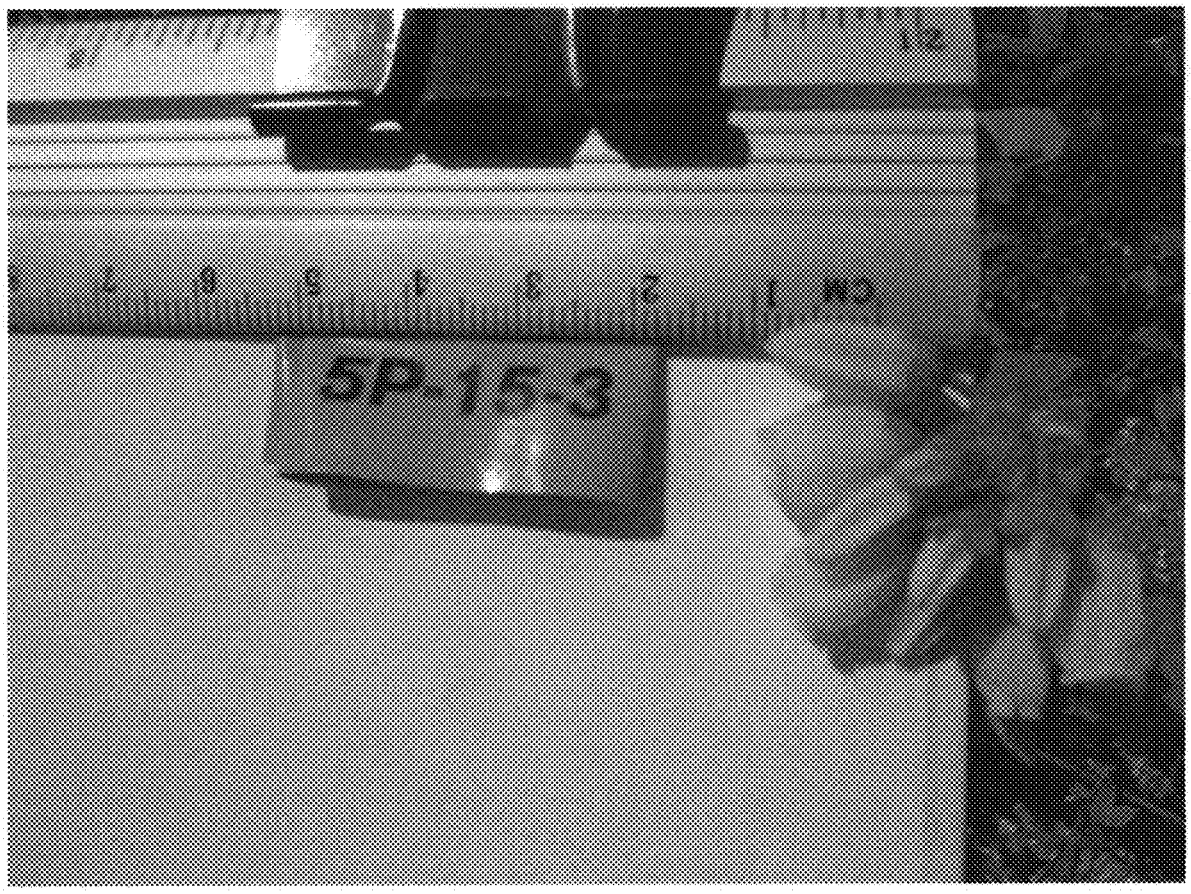
FIG. 3 is a photograph of the flowers of the new variety 'MG07876-15-003' at approximately 6 years of age.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'MG07876-15-003'. The data which defines these characteristics was collected from asexual reproductions of the original selection. Dimensions, sizes, colors, and other characteristics are approximations and averages set forth as accurately as possible. The plant history was taken on plants approximately 3 years of age, and the descriptions relate to plants grown in the field in Moondarra, Victoria, Australia. Descriptions of fruit characteristics were made on fruit grown in Moondarra, Victoria, Australia. Color designations are from Pantone Color Bridge plus.

Classification:

*a. Family.*—Ericaceae.
*b. Genus.*—*Vaccinium.*
*c. Species.*—hybrid.
*d. Common name.*—Blueberry.

Parentage:

*Female parent.*—'Elliott' (not patented).
*Male parent.*—'Caroline' (not patented).

Market class: A fruiting plant intended for the fresh fruit market.

PLANT

General:

*a. Parentage.*—'Elliott' x 'Caroline'.
*b. Plant height.*—0.9-1.2 m.
*c. Plant width.*—~0.7-0.8 m.
*d. Growth habit.*—Upright/whippy.
*e. Growth (vigor).*—Strong to very strong.
*f. Productivity.*—Medium to high (~6.6 kg/plant).
*g. Cold hardiness.*—Not tested.
*h. Cold tolerance.*—Not tested.
*i. Chilling requirement.*—Not tested.
*j. Tolerance to disease.*—Not tested.
*k. Leafing.*—Strong to very strong.
*l. Twigginess.*—Moderate.

STEM

General:

*a. Suckering tendency.*—7-8/plant.
*b. Mature cane color.*—165A/161D-164C.
*c. Mature cane length.*—~0.9 m.
*d. Mature cane width.*—1.1 cm.
*e. Bark texture.*—Medium roughness.
*f. Fall color on new shoots.*—N/A.
*g. Surface texture of new wood.*—Smooth.
*h. Internode length on strong, new shoots.*—~20 mm.
*i. Fruiting wood.*—Up to 18 cm in length.

FOLIAGE

General:

*a. Time of beginning of leaf bud burst.*—Approximately mid-October.
*b. Leaf color (top side).*—135B/137A.
*c. Leaf color (under side).*—145B/138D.
*d. Leaf arrangement.*—Alternate.
*e. Leaf shape.*—Elliptic.
*f. Leaf margins.*—Entire.
*g. Undulation of margin.*—Weak.
*h. Leaf venation.*—Reticulate.
*i. Leaf apices.*—Acute.
*j. Leaf bases.*—Obtuse.
*k. Leaf length.*—66-79 mm.
*l. Leaf width.*—35-38 mm.
*m. Leaf length/width ratio.*—Medium; 1:0.53-1:0.48.
*n. Leaf nectarines.*—Absent.
*o. Pubescence of upper side.*—Absent.
*p. Pubescence of lower side.*—Absent.
*q. Cross sectional profile.*—Flat.
*r. Longitudinal profile.*—Straight.
*s. Attitude.*—Semi-upright.

Petioles:

*a. Length.*—4-6 mm.
*b. Width.*—1.5 mm.
*c. Color.*—Yellow-Green 144D.

FLOWERS

General:

*a. Time of beginning of flowering.*—19$^{th}$ October.
*b. Time of 50% anthesis.*—27$^{th}$ October.
*c. Flower shape.*—Urceolate.
*d. Flower bud density.*—Moderate to high.
*e. Flower fragrance.*—Weak; sweet smell.

Corolla:

*a. Length.*—11-13 mm.
*b. Width.*—5-6 mm.
*c. Aperture width.*—Approximately 5 mm.
*d. Anthocyanin coloration of corolla.*—Absent.
*e. Corolla ridges.*—Present.
*f. Protrusion of stigma.*—Absent.

Inflorescence:

*a. Length.*—~26 mm.
*b. Diameter.*—~35-40 mm.
*c. Surface texture of peduncle.*—Smooth.
*d. Surface texture of pedicel.*—Smooth.
*e. Color of pedicel.*—146C/144A.
*f. Number of flowers per cluster.*—Approximately 8-10.
*g. Flower cluster density.*—Moderate.

Calyx (with sepals):

*a. Diameter.*—6-7 mm.

*b. Color* (*sepals*).—176C/145B.

Stamen:

*a. Length.*—7-8 mm.

*b. Number per flower.*—Approximately 10.

*c. Filament color.*—145D/142C.

*d. Style length.*—8-9 mm.

*e. Color.*—N144A/C.

Style:

*a. Length.*—8-9 mm.

*b. Color.*—N144A/C.

Pistil:

*a. Length.*—11-12 mm.

*b. Ovary color* (*exterior*).—144A/135B.

Anther:

*a. Length.*—4-5 mm.

*b. Number.*—Approximately 10.

*c. Color.*—165B.

Pollen:

*Self-compatibility.*—Yes (100%).

FRUIT

General:

*a. Time of fruit ripening.*—Very late; February to March in Moondarra, Victoria, Australia.

*b. Time of* 50% *maturity.*—Late February.

*c. Fruit development period.*—Approximately 90-100 days.

*d. Cluster density.*—~24 berries per cluster.

*e. Unripe fruit color.*—N144D.

*f. Ripe berry color.*—203C.

*g. Berry surface wax abundance.*—Moderate.

*h. Berry flesh color.*—145D.

*i. Berry weight.*—1.5-2.5 g.

*j. Berry height from calyx to scar.*—12-15 mm.

*k. Berry diameter.*—18-20 mm.

*l. Berry shape.*—Oblate.

*m. Fruit stem scar.*—Small, dry.

*n. Sweetness when ripe.*—Medium.

*o. Firmness when ripe.*—Firm.

*p. Acidity when ripe.*—Low to medium.

*q. Storage quality.*—Good.

*r. Suitability for mechanical harvesting.*—N/A.

*s. Self-fruitfulness.*—Yes.

*t. Uses.*—Fresh fruit.

*u. Type.*—On one-year-old shoots only.

SEED

General:

*a. Seed abundance in fruit.*—Moderate.

*b. Seed color.*—167A/164A.

*c. Seed length.*—~1 mm.

COMPARISON BETWEEN COMMERCIAL CULTIVARS

| Organ | Context | 'MG07876-15-003' | 'Brigitta' (not patented) | 'Ridley 0808' (U.S. Plant Pat. No. 31,074) |
|---|---|---|---|---|
| Plant | Vigor | Strong | Medium | Strong |
| Plant | Growth habit | Semi-upright | Upright | Upright |
| One-year-old shoot | Color | Green | Green | Green |
| One-year-old shoot | Length of internode | Medium | Medium | Medium to long |
| Leaf | Length | Long; 66-79 | Long | Medium to long |
| Leaf | Width | Broad | Broad | Broad |
| Leaf | Shape | Elliptic | Elliptic | Elliptic |
| Leaf | Color of upper side | Green; 135B/137A | Green | Green |
| Leaf | Intensity of green color on upper side (varieties with green leaf color only) | Light-medium | Medium | Medium |
| Leaf | Margin | Entire | Serrate | Entire |
| Flower bud | Anthocyanin coloration | Medium-strong | Medium-strong | Medium |
| Flower | Shape of corolla | Urceolate | Urceolate | Urceolate |
| Flower | Size of corolla tube | Medium | Medium | Medium |
| Flower | Anthocyanin coloration of corolla tube | Absent or very weak | Absent or very weak | Absent or very weak |
| Flower | Ridges on corolla tube | Present | Present | Present |
| Fruit cluster | Density | Dense | Medium-dense | Medium |
| Unripe fruit | Intensity of green color | Light-medium; N144D | Light | Light |
| Fruit | Size | Large; 18-20 mm | Medium | Medium to large |
| Fruit | Shape in longitudinal section | Oblate | Oblate | Oblate |
| Fruit | Attitude of sepals | Erect | Erect | Erect |
| Fruit | Diameter of calyx basin | Small-medium | Small-medium | Large to very large |
| Fruit | Depth of calyx basin | Medium-deep | Deep | Deep |
| Fruit | Intensity of bloom | Medium | Medium | Strong |
| Fruit | Color of skin | Dark blue; 203C | Dark blue | Dark blue |
| Fruit | Firmness | Firm | Medium | Very firm |
| Fruit | Sweetness | Medium-high | Low-medium | Very high |
| Fruit | Acidity | Low-medium | Low-medium | Medium to high |
| Time of | Vegetative bud burst | Late | Medium | Medium to late |
| Time of | Beginning of flowering | Late | Medium | Medium to late |
| Time of | Beginning of fruit ripening | Very late | Medium | Medium to late |

The invention claimed is:

1. A new and distinct variety of blueberry plant named 'MG07876-15-003', substantially as illustrated and described herein.

* * * * *